United States Patent [19]

Davies et al.

[11] Patent Number: 5,304,481
[45] Date of Patent: Apr. 19, 1994

[54] PLANT THIOESTERASE HAVING PREFERENTIAL HYDROLASE ACTIVITY TOWARD C12 ACYL-ACP SUBSTRATE

[75] Inventors: Huw M. Davies; Michael R. Pollard, both of Davis, Calif.

[73] Assignee: Calgene, Inc., Davis, Calif.

[21] Appl. No.: 973,935

[22] Filed: Nov. 10, 1992

Related U.S. Application Data

[63] Continuation of Ser. No. 514,030, Apr. 26, 1990, abandoned.

[51] Int. Cl.$^5$ .......................... C12N 9/16; C12P 7/62
[52] U.S. Cl. .................................. 435/196; 435/135
[58] Field of Search ............................... 435/196, 135

[56] References Cited

FOREIGN PATENT DOCUMENTS 0255378 2/1988 European Pat. Off. .
0323753 7/1989 European Pat. Off. .

OTHER PUBLICATIONS

Pollard, et al., "A Specific Acyl-ACP Thioesterase Implicated In Medium-Chain Fatty Acid Production In Immature Cotyledons of *Umbellulaira californica*," Archives of Biochem. and Biophysics (1991) 284(2):306–312.

Witkowski, et al., "Molecular Cloning and Sequencing of a cDNA Encoding The Acyl Carrier Protein and its Flanking domains In the Mammalian Fatty Acid Synthetase," *Eur. J. Biochem.* (1987) 165:601–606.

Murphy, et al., "Solubilization, Purification and Kinetic Properties of Three Membrane-Bound Long-Chain Acyl-Coenzyme-A Thioesterases From Microsomes of Photosynthetic Tissue," *Eur. J. Biochem.* (1984) 142:43–48.

McKeon, et al., "Purification and Characterization of the Stearoyl-Acyl Carrier Protein Desaturase and the Acyl-Acyl Carrier Protein Thioesterase From Maturing Seeds of Safflower," *J. of Bio. Chem.*, (1982) 257(20):12141–12147.

Shine, et al., "Fat Metabolism In Higher Plants," *Archives of Biochem. and Biophysics* (1976) 172:110–116.

Slabas, et al., "Enzymology and Molecular Biology of Plant Lipid Biosynthesis," *J. Experimental Botany* (1990) 41:P8–2.

Gould, et al., "Use of the DNA Polymerase Chain Reaction for Homology Probing: Isolation of Partial cDNA or Genomic Clones Encoding the Iron–Sulfur Protein of Succinate Dehydrogenase From Several Species," *Proc. Natl. Acad. Sci. USA* (1989) 86:1934–1938.

Gasser, et al., "Genetically Engineering Plants For Crop Improvement," *Science* (1989) 244:1293–1299.

Jaworski et al., *Differences in Leaf Intumes . . . /Hort Science, vol. 23, No. 5, 1988.*

Tinnin et al., *The Allelopathic Influence . . . /* For. Sci., vol. 31, No. 4, 1985.

Harwood, "Lipid Metabolism in Plants," *Critical Reviews in Plant Sciences* (1989) 8:1–43.

Harwood, "Fatty Acid Metabolism," *Ann. Rev. Plant Physiol. Plant Mol. Biol.* (1988) 39:101–138.

Pollard and Singh, "Fatty Acid Synthesis in Developing Oilseeds," *The Metabolism, Structure and Function of Plant Lipids,* 1987, pp. 455–463.

Stumpf, "The Biosynthesis of Saturated Fatty Acids," *The Biochemistry of Plants,* (1987) 9:121–136.

(List continued on next page.)

*Primary Examiner*—David M. Naff
*Assistant Examiner*—Michael V. Meller

[57] ABSTRACT

This invention relates to a novel class of plant enzymes, thioesterases having preferential hydrolase activity toward one or more medium-chain acyl-ACP substrates. Purification, especially the removal of substantially all other plant proteins, and use of the plant thioesterase is provided, including the use of the protein as a tool in gene isolation for biotechnological applications and a description of various uses for such nucleic acid sequences thereto. The enzyme is preferably obtained from *Umbellularia californica* and has preferential hydrolase activity toward C12 acyl-ACP substrate.

11 Claims, No Drawings

OTHER PUBLICATIONS

Naggert, et al., "Cloning and Sequencing of the Meidum-Chain S-Acyl Fatty Acid Synthetase Thioester Hydrolase cDNA From Rat Mammary Gland," *Biochem. J.* (1987) 243:597–601.

Poulose, et al., "Cloning and Sequencing of the cNDA for S-Acyl Fatty Acid Synthase Thioesterase from the Uropygial Gland of Mallard Duck", *J. Biol. Chem.* (1985) 260:15953–15958.

Ohlrogge, et al., "Fat Metabolism in Higher Plants," *Archives of Biochemistry and Biophysics* (1978) 2:382–391.

OO and Stumpf, "Fatty Acid Biosynthesis in the Developing Endosperm of *Cocos nucifera*," *Lipids* (1979) 14:132–143.

Pollard, FIGS. 1 through 5 representing information presented as slides at the Seventh International Symposium of Plant Lipids, held Jul. 27–Aug. 1, 1986 at the University of California, Davis, Calif.

Battey et al., "Genetic Engineering for Plant Oils: Potential and Limitations", *Trends in Biotechnology* (1989) 7:122–126.

Bayley, et al., "Metabolic consequences of Expression of the Medium Chain Hydrolase Gene of The Rat In Mouse NIH 3T3 Cells," *Bio/Tech* (1988) 6:1219–1221.

Downey, et al., "Genetic Control of Fatty Acid Composition In Oilseed Crops," *Proceedings of the Flax Institute USA* (1971) 41(3):1–3.

Knauf, et al., "Reprogramming Levels of Fatty Acid Synthesis Enzymes In Developing Embryos of Rapeseed," *J. Cell Biochem. Suppl.* (1990) 14E:266.

Bafor, et al., "Properties of the Glycerol Acylating Enzymes in Microsomal Preparations from the Developing Seeds of Safflower (*Carthamus tinctorius*) and Turnip Rape (*Brassica campestris*) and their Ability to Assemble Cocoa-Butter Type Fats," *JAOCS* (1990) 67(4):217–255.

Battey, et al., "Genetic engineering for plant oils: potential and limitation," *TIBTECH* (1989) 7:122–126.

Knauf, V., "The application of genetic engineering to oilseed crops," *TIBTECH* (1987) 5:40–47.

PLANT THIOESTERASE HAVING PREFERENTIAL HYDROLASE ACTIVITY TOWARD C12 ACYL-ACP SUBSTRATE

This is a continuation of application Ser. No. 07/514,030, filed Apr. 26, 1990, now abandoned.

TECHNICAL FIELD

The present invention is directed to a protein relevant to synthesis of medium chain fatty acids in plants and methods of use related to the protein and related nucleic acid sequences.

BACKGROUND

Improved means to manipulate fatty acid compositions, from biosynthetic or natural plant sources, are needed. For example, novel oil products, improved sources of synthetic triacylglycerols (triglycerides), alternative sources of commercial oils, especially tropical oils (i.e., palm kernel and coconut oils), and plant oils found in trace amounts from natural sources are desired for a variety of industrial and food uses.

To this end, the Fatty Acid Synthetase (FAS) system in higher plants has been studied. The mechanism of production of "long-chain fatty acids", i.e., fatty acids having a carbon chain length of equal to or greater than 16 carbon atoms (C16), via the acyl carrier protein (ACP)-dependent, plastid-localized FAS of plants is relatively well characterized. However, the mechanism(s) by which plants produce fatty acids having shorter carbon chains, i.e., less than C16 atoms, has remained elusive until the invention described herein.

Medium-chain fatty acids (C8 to C14) are found in some natural plant species in abundance. For example, several species in the genus Cuphea accumulate triglycerides containing medium-chain fatty acids, e.g., *Cuphea procumbens, Cuphea lutea* and *Cuphea inflata.* Another known natural plant source of medium-chain fatty acids is the *Lauraceae* family: e.g., the California Bay (*Umbellularia californica*), Pisa (*Actinodophne hookeri*) and Sweet Bay (*Laurus nobilis*) trees. Other plant sources include Ulmaceae (elm), Myristicaceae, Simarubaceae, Vochysiaceae, and Salvadoraceae.

Medium-chain fatty acids have special importance in the detergent and lubricant industries or in the formulation of edible oils with reduced caloric value or other health benefits. See for example, U.S. Pat. No. 4,863,753 and Barch, A. C. & Babayan, V. K., Am. J. Clin. Nat. (1982) 36:950–962.

As such, a ready source of medium-chain fatty acids, including storage lipids which have incorporated one or more medium-chain fatty acids therein, are desired for a variety of industrial and food use fields. Once the biosynthetic pathway of medium-chain fatty acids in plants is determined, the system can be studied for application in vivo and in vitro. Studies of the mechanism may provide means to further enhance, control, modify or otherwise alter medium-chain fatty acid products or resulting triglycerides and oils. Thus, the elucidation of the factor(s) critical to the natural production of medium-chain fatty acids in plants is desired, including the purification of such factors and the characterization of element(s) and/or co-factors which enhance the efficiency of the system. Of special interest are the nucleic acid sequences corresponding to factors related to the production of such medium-chain fatty acids for applications in genetic engineering.

Relevant Literature

P. K. Stumpf, *The Biochemistry of Plants* (P. K. Stumpf & E. Conn, eds.) (1987) 9:121–136, summarizes theoretical mechanisms of termination of the fatty acid chain elongation pathway producing medium-chain fatty acids in plants. Specific thioesterases are postulated as well as other possible explanations. Harwood, J. L., *Ann. Rev. Plant Physiol. Mol. Bio.* (1988) 39:101–138, references various possibilities in the literature regarding production of large amounts of medium-chain length fatty acids in plant tissues and reports that all attempts to find a "suitable thioesterase" responsible for medium-chain fatty acid production have proved negative. Harwood, J. L., *Crit. Rev. Plant Sci.* (1989) 8:1–43, reviews current information regarding the production of medium-chain fatty acids in plants with the conclusion that very little is known. See also, Pollard, M. R. and Singh, S. S., *The Metabolsim, Structure and Function of Plant Lipids,* Stumpf, P. K., Mudd, J. B., and Nes, W. D., eds. (Plenum Press, N.Y. 1987) pp. 455–463.

SUMMARY OF THE INVENTION

By this invention, the existence of a heretofore unproven factor critical to the biosynthesis of medium-chain fatty acids in plants is demonstrated. Particularly, this invention relates to a novel class of plant enzymes, thioesterases having preferential hydrolase activity toward one or more medium-chain acyl-ACP substrates. Purification, especially the removal of substantially all other plant proteins, and use of the plant thioesterase is provided, including the use of the protein as a tool in gene isolation for biotechnological applications and a description of various uses for such nucleic acid sequences thereto.

Thus, in a first aspect, this invention relates to a partially purified thioesterase being substantially free from other plant proteins. In a preferred embodiment, the plant thioesterase demonstrates preferential hydrolase activity to dodeconoyl ("lauroyl," "lauryl")-ACP (C12) and/or decanoyl("capryl")-ACP (C10) acid. Partially purified plant thioesterases having preferential hydrolase activity toward one or more medium-chain fatty acids are described.

In a different aspect of this invention, DNA sequences related to the plant thioesterases of this invention are described, with details regarding methods to obtain such sequences and their use.

In a further aspect of this invention, methods of producing medium-chain free fatty acids utilizing a plant thioesterase having preferential hydrolase activity towards medium-chain fatty acids are described.

In yet a different aspect of this invention, it should be recognized that the plant thioesterases of this invention have implications related to the production of medium-chain triglycerides (MCT's) as well. A triglyceride having one or more medium-chain fatty acids incorporated into any position of the triglyceride glycerol backbone is defined as an MCT. Thus, the medium-chain fatty acids may be incorporated into triglycerides in vitro and in vivo offering the opportunity to increase the ratio of medium-chain fatty acids as to long-chain fatty acids and thereby modify triglyceride fatty acid composition.

DETAILED DESCRIPTION OF THE INVENTION

A plant thioesterase of this invention includes any sequence of amino acids, such as a protein, polypeptide, or peptide fragment, which demonstrates the ability to catalyze the production of medium-chain free fatty acid(s) and ACP from medium-chain acyl ACP's. During biosynthesis of lipids in a plant cell, fatty acids are typically covalengly bound to ACP or coenzyme A (CoA) carriers. The release of medium-chain free fatty acids via hydrolysis of the thioester acyl-ACP bond is therefore of interest for the controlled production of medium-chain free fatty acids. As de novo fatty acid synthesis in plants is ACP-dependent, there is special interest in plant thioesterases which demonstrate preferential activity toward ACP-bound medium-chains while having little or no activity on fatty acids bound to CoA.

With the identification and characterization of this new class of enzyme, it will be apparent to those skilled in the art that such plant thioesterases may be obtained from a variety of sources natural and synthetic. The determination that specific plant thioesterases are involved in the production of medium-chain fatty acids thus offers many possibilities for plant sources. Plants having significant presence of medium-chain fatty acids therein are preferred candidates to obtain naturally-derived plant thioesterases. In addition, the naturally-derived plant thioesterase then provides opportunities to modify such amino acid sequences and starting materials for synthetic-protein modeling. Modified amino acid sequences include sequences which have been mutated, truncated, increased and the like, whether such sequences were partially or wholly synthesized. Sequences which are actually purified from plant preparations and identical thereto, are equally considered naturally derived. Moreover, by the identification of this factor, plant thioesterases can now be used to investigate chain termination events of plant fatty acid biosynthesis in general. For example a plant thioesterase can be used in conjunction with plastid lysates to enhance the production and/or modify the composition of the fatty acids prepared in vitro. Because all higher plants appear to synthesize fatty acids via a common metabolic pathway, the study and/or application of one plant thioesterase to a heterologous plant host may be readily achieved in a variety of species.

Medium-chain-preferring acyl-ACP plant thioesterases have been partially purified from immature embryos of the California Bay (*Umbellularia californica*) tree, hereinafter sometimes referred to as "Bay," and *Cuphea hookeriana*, hereinafter sometimes referred to as "Cuphea." As noted above, other plant sources may also provide sources for this enzyme. Plant thioesterases are obtainable from Bay, Cuphea, and from other plant derivatives through the use of protein purification, nucleic acid probes, antibody preparations, protein modeling, or sequence comparisons, for example. Of special interest are the respective amino acid and nucleic acid sequences corresponding to such plant thioesterases. Once nucleic acid sequence is obtained for the given plant thioesterase, further plant sequences may be compared and/or probed to obtain homologously related DNA sequences thereto. Especially of interest are plant thioesterases which demonstrate preferential hydrolase activity toward lauroyl-ACP or decanoyl-ACP.

By "C12 preferring" is meant that the hydrolytic activity of the enzyme preparation demonstrates a preference for laurate, and perhaps decanoate, over other substrates of different acyl carbon lengths. In a like fashion, a plant thioesterase having "C10 preferring" activity will show higher levels of activity toward decanoate substrates, and perhaps oceneate, over other substrates of different acyl carbon lengths. It is noted that some activity, of a significantly lesser magnitude, may be observed against other fatty acid substrates, i.e., the specificity will be substantial, but may not be absolute.

A plant thioesterase of this invention will display activity toward acyl-ACP substrates (i.e., Cuphea C10-preferring acyl-ACP thioesterase) and may, in fact, demonstrate a marked preference for acyl-ACP substrates over acyl-CoA substrates (i.e., Bay C12-preferring acyl-ACP thioesterase). Plant thioesterases which display preferential activity toward acyl-ACP substrates are especially preferred because they are likely to be closely associated with the fatty acid synthesis pathway in immature embryo plastids. However, activity toward acyl-CoA substrates or other, synthetic substrates, is also contemplated herein.

As demonstrated more fully in the Examples, a plant thioesterase preparation having preferential hydrolase activity toward medium-chain fatty acyl-ACP substrates of California Bay substantially free of other plant proteins is obtainable as follows: Briefly, a supernatant fraction of ground California Bay immature embryos is subjected to ammonium sulfate fractionation, followed by hydroxyapatite column chromatography to the redissolved pellet, applying carboxymethyl Sepharose chromatography to the eluted fractions, and further chromatography on a column of immobilized *E. coli* ACP. The resulting partially purified preparation maybe characterized by various parameters, including molecular weight.

Also described in the Examples, are methods to obtain a partially purified Cuphea C10-preferring acyl-ACP thioesterase. The Cuphea thioesterase is partially purified from other plant proteins in the same general manner as the Bay in that a supernatant fraction of ground *Cuphea hookeriana* seeds are subjected to an amonium sulfate fractionation, followed by hydroxyapatite column chromotagraphy to the redissolved pellet. As described more fully in the Examples, the various buffers are different than those used in the Bay extraction. Although the resulting Cuphea preparation also demonstrates activity against longer-chain substrate in addition to medium-chain fatty acid acyl-ACP substrate, both above described Bay and Cuphea preparations are considered to be "substantially free from other plant proteins" in that they demonstrate a recognizably distinct preferential activity toward medium-chain fatty acid acyl-ACP substrates.

As for both the Cuphea and Bay preparations, additional and/or alternative purification steps may be desired to purify the protein extract to homogeneity, to increase yield o the like. Moreover, now that the existence of these proteins are confirmed and various properties described, alternative purification protocols and/or additional purification steps are within the capabilities of one skilled in the art. It is noted that both the Bay and Cuphea thioesterase preparations show lowered concentration by extensive contact with glass and plastic surfaces. This is effectively prevented by the inclusion of detergents such as Triton X100 or CHAPS in the column and assay buffers. Many such detergents are stimulatory in the assay.

Once the plant thioesterase is obtained, it may be used to obtain its corresponding amino acid and/or nucleic acid sequences thereto. For sequencing, the use of a two-dimensional gel may be desired over a one dimensional SDS-PAGE gel. As a representative example, the amino acid sequence may be obtained by the sequencing of peptide fragments resulting from partial protease digestion of protein blots recovered from the gel. The peptide fragments may be used to deduce amino acid sequences and eventually, amino acid sequence may be obtained. From the amino acid sequence information, nucleic acid probes can be constructed for use in polymerase chain reaction (PCR) process for the construction of probes to be used in the recovery of the gene. As yet a different example, the purified protein may be used to raise antibodies thereto. The antibodies, polyclonal or monoclonal, may also be used to isolate other immunologically related plant thioesterase genes. Alternative methods will be apparent in accordance with methods familiar to those skilled in the art.

The nucleic acid sequences which encode plant thioesterases may be used in various constructs, for example as probes to obtain further sequences or in conjunction with an expression cassette to increase levels of the respective medium-chain preferring acyl-ACP thioesterase of interest in a host cell for recovery or study of the enzyme in vitro or in vivo. Especially of interest is the expression of a C12-preferring or C10-preferring acyl-ACP thioesterase in a plant host cell, to modify the composition of fatty acids and/or triglycerides found therein. By increasing the amount of respective thioesterase available to the plant fatty acid synthetase complex, an increased percentage of shorter chain fatty acids may be provided. In a like manner, for some applications it may be desired to decrease the amount of medium-chain preferring acyl-ACP thioesterase expressed in a plant cell by anti-sense technology, for example. See, co-pending U.S. patent application Ser. No. 240,408 filed Mar. 30, 1988.

A DNA sequence encoding a plant thioesterase of this invention may include genomic or cDNA sequence. A cDNA sequence may or may not contain pre-processing sequences, such as transit peptide sequences. Transit peptide sequences facilitate the delivery of the protein to a given organelle and are cleaved from the amino acid moiety upon entry into the organelle, releasing the "mature" sequence. The use of the precursor cDNA sequence is preferred in plant cell expression cassettes. Other transit peptide sequences may be employed to translocate the plant acyl-ACP thioesterase of this invention to various organelles of interest. See, European Patent Application Publication No. 189,707.

Furthermore, the complete genomic sequence of the plant thioesterase may be obtained by the screening of a genomic library with a cDNA probe and isolating those sequences which regulate expression in seed tissue. In this manner, the transcription and translation initiation regions, regulatory introns, and/or transcript termination regions of the plant thioesterase may be obtained for use in a variety of DNA constructs, with or without the thioesterase structural gene. Thus, nucleic acid sequences corresponding to the plant thioesterase of this invention may also provide signal sequences useful to direct transport into a plastid, 5' upstream non-coding regulatory regions (promoters) having useful tissue and timing profiles, and may lend insight into other features of the gene.

Other nucleic acid sequences homologously related to DNA sequences encoding such plant thioesterases are also provided herein. One skilled in the art will readily recognize that antibody preparations, nucleic acid probes (DNA and RNA) and the like may be prepared and used to screen and recover medium-chain-preferring acyl-ACP thioesterases from other plant sources.

Typically, a homologously related nucleic acid sequence will show at least about 60% homology, and more preferably at least about 70% homology, between the target sequence and the given plant thioesterase of interest, excluding any deletions which may be present. Homology is found when there is an identity of base sequence and may be determined upon comparison of sequence information, nuclei acid or amino acid, or through hybridization reactions conducted under relatively stringent conditions, e.g., having a fairly low percentage of non-specific binding with thioesterase probes.

Probes can be considerably shorter than the entire sequence, but should be at least about 10, preferably at least about 15, more preferably at least 20 nucleotides in length. Longer oligonucleotides are also useful, up to the full length of the gene encoding the polypeptide of interest. Both DNA and RNA probes can be used.

A genomic library prepared from the plant source of interest may be probed with conserved sequences from the plant thioesterase to identify homologously related sequences. Use of the entire cDNA may be employed if shorter probe sequences are not identified. Positive clones are then analyzed by restriction enzyme digestion and/or sequencing. In this general manner, one or more sequences may be identified providing both the coding region, as well as the transcriptional regulatory elements of the thioesterase gene from such plant source.

Once the desired plant thioesterase sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized, where one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The DNA sequence encoding a plant thioesterase of this invention may be combined with other, i.e. "heterologous," DNA sequences in a variety of ways. By heterologous DNA sequences is meant any DNA sequence which is not naturally found joined to the plant thioesterase, including combinations of DNA sequences from the same plant which are not naturally found joined together.

In vitro prepared plant expression constructs having a plant thioesterase as the DNA sequence of interest for expression thereof may be employed with a wide variety of plant life, particularly, plant life involved in the production of vegetable oils for edible and industrial uses. Most especially preferred are temperate oilseed crops. Plants of interest include but are not limited to rapeseed (Canola and High Erucic Acid varieties), sunflower, safflower, cotton, Cuphea, soybean, peanut, coconut and oil palms, and corn. Depending on the method for introducing the DNA expression constructs ino the host cell, other DNA sequences may be required. Importantly, this invention is applicable to dicotyledyons and monocotyledons species alike and will be readily applicable to new and/or improved transformation and regulation techniques.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed with allow for the transformation of various monocot and dicot plant species.

The DNA sequence encoding a plant thioesterase of this invention may be employed in conjunction with all or part of the gene sequences normally associated with the thioesterase. In its component parts, a DNA sequence encodes thioesterase is combined in a DNA construct having, in the 5' to 3' direction of transcription, a transcription initiation control region capable of promoting transcription and translation in a host cell, the DNA sequence encoding plant thioesterase and a transcription and translation termination region.

Depending upon the host, the regulatory regions will vary, including regions from structural gene from viral, plasmid or chromosomal genes, or the like. For expression in prokaryotic or eukaryotic microorganisms, particularly unicellular hosts, a wide variety of constitutive or regulatable promoters may be employed. In these instances, the primary purposes for the preparation of the plant is the use of the enzyme for in vitro applications. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the constructs will involve regulatory regions functional in plants which provide for modified production of plant thioesterase and/or modification of the fatty acid composition. The open reading frame, coding for the plant thioesterase or functional fragment thereof will be joined at its 5' end to a transcription initiation regulatory region such as the wildtype sequence naturally found 5' upstream to the thioesterase structural gene. Numerous other transcription initiation regions are available which provide for a wide variety of constitutive or regulatable, e.g., inducible, transcription of the structural gene functions. Among transcriptional initiation regions used for plants are such regions associated with the structural genes such as for nopaline, mannopine or with napin, acyl carrier protein (ACP) promoters and the like. The transcription/translation initiation regions corresponding to such structural genes are found immediately 5' upstream to the respective start codons. In embodiments wherein the expression of the thioesterase protein is desired in a plant host, the use of all or part of the complete plant thioesterase gene is desired; namely the 5' upstream non-coding regions (promoter) together with the structural gene sequence and 3' downstream non-coding regions may be employed. If a different promoter is desired, such as a promoter native to the plant host of interest or a modified promoter, i.e., having transcription initiation regions derived from one gene source and translation initiation regions derived from a different gene source or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 147,781, filed Jan. 25, 1988, and U.S. Ser. No. (unassigned) filed on or about Mar. 16, 1990 having a title "Novel Sequences Preferentially Expressed In Early Seed Development and Methods Related Thereto" which is hereby incorporated by reference. Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the plant thioesterase or a convenient transcription termination region derived from a different gene source, especially the transcript termination region which is naturally associated with the transcript initiation region. The transcript termination region will contain at least about 1 kb, preferably about 3 kb of sequence 3' to the structural gene from which the termination region is derived.

In developing the DNA construct, the various components of the construct or fragments therefore will normally be inserted into a convenient cloning vector which is capable of replication in a bacterial host, e.g., *E. coli*. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Depending upon the number of different host species the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence. When a DNA sequence encoding a plant thioesterase is to be expressed in a plant host cell, the use of "plant preferred codons" is desirable.

As mentioned above, the manner in which the DNA construct is introduced into the plant host is not critical to this invention. Any method which provides for efficient transformation may be employed. Various methods for plant cell transformation include the use of Ti- or Ri-plasmids, microinjection, electroporation, DNA particle bombardment, liposome fusion, DNA bombardment or the like. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where the Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall formation), the latter being permissible, so long as the vir genes are present in the transformed host. The armed plasmid can give a mixture of normal plant cell and gall.

In some instances where Agrobacterium is used as the vehicle for transforming plant cells, the expression construct bordered by the T-DNA border(s) will be inserted into a broad host spectrum vector, there being broad host spectrum vectors described in the literature. Commonly used is pRK2 or derivatives thereof. See, for example, Ditta et al., PNAS USA, (1980) 77:7347-7351 and EPA 0 120 515, which are incorporated herein by reference. Included with the expression construct and the T-DNA will be one or more markers, which allow for selection of transformed Agrobacterium and transformed plant cells. A number of markers have been developed for use with plant cells, such as resistance to chloramphenicol, the aminoglycoside G418, hygromycin, or the like. The particular marker employed is not essential to this invention, one or another marker being preferred depending on the particular host and the manner of construction.

For transformation of plant cells using Agrobacterium, explants may be combined and incubated with the transformed Agrobacterium for sufficient time for transformation, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

EXAMPLES

In the experimental disclosure which follows, all temperatures are given in degrees centigrade (°), weights are given in grams (g), milligram (mg) or micrograms ($\mu$g), concentrations are given as molar (M), millimolar (mM) or micromolar ($\mu$M) and all volumes are given in liters (l), microliters ($\mu$l) or milliliters (ml), unless otherwise indicated.

EXAMPLE 1—Bay Thioesterse Assay

To assay for C12 thioesterase activity the following mixture is incubated at 30° for 30 min: "buffer" comprising 7mM $KH_2PO_4$-KOH pH 8, 20% v/v glycerol, 1 mM dithiothreitol (DTT), 0.1% v/v/ Triton X100; extract of immature *Umbellularia californica* ("Bay") seeds in the same or very similar buffer or in an "extraction buffer" as described in Example 2; and 5 $\mu$l of $^{14}$C-radiolabeled lauroyl-ACP substrate for a total volume of 100 $\mu$l and final lauroyl-ACP concentration of 0.5 $\mu$M. Lauroyl-ACP substrate is prepared according to the method of Rock et al (*Methods in Enzymology* (1981) 72:397-403), using ACP prepared from *Escherichia coli* by the method of Rock and Cronan (*Methods in Enzymology* (1981) 71:341-351). The laurate is radiolabeled in the carboxylate group at a specific radioactivity of 50-60 $\mu$Ci/$\mu$mol.

The reaction is stopped by adding 0.5 ml cold (0°) 10% v/v acetic acid. The fatty acid product of the hydrolytic enzyme action is extracted away from the unhydrolyzed substrate by adding 1 ml diethyl ether and mixing vigorously. After settling for a few minutes the upper ether layer is transferred to 5ml scintillation fluid for determination of radioactivity by liquid scintillation spectrometry. Additional ether extractions may be performed to recover remaining traces of the reaction product for more accurate quantitation of the enzyme activity if desired. The amount of ether-extracted radioactivity is a direct measure of C12-preferring acyl-ACP thioesterase activity, provided the amount of enzyme is not sufficient t hydrolyze more than about 25% of the substrate. With greater activity than this the relationship between radioactivity in the ether layer and the quantity of enzyme becomes markedly nonlinear. The enzyme preparation must then be diluted appropriately to bring the activity into the linear range of the assay.

The activity is confirmed to be thioesterase by analysis of the ether-soluble product using thin-layer chromatography (TLC). The product co-migrates with authentic laurate on a silica TLC plate (solvent: 80% hexane, 20% diethyl ether, 1% acetic acid v/v). If phenacyl esters are prepared (Borch, R. F., *Analytical Chemistry* (1975) 47:2437-2439) using the ether product-containing layer from the assay procedure, the resulting radioactive spot co-migrates with authentic lauroyl phenacyl ester on a C18 TLC plate (solvent: 100% methanol), as does the product of base hydrolysis of the lauroyl-ACP substrate. These observations verify that the ether-extracted product of the enzyme reaction is free laurate. It is also deduced that the enzyme of interest hydrolyzes the thioester bond, e.g. it cannot be a protease attacking the ACP moiety of the substrate or the product would be lauroyl-phosphopantetheine which would have migrated differently on TLC.

EXAMPLE 2—Bay Thioesterase Purification & Identification

Immature seeds of *Umbellularia californica* ("Bay") are harvested at the stage at which decanoate and laurate predominate in the fatty acid composition as determined by total fatty acid analysis of the cotyledons. The cotyledons from such seeds are dissected from the other seed parts and stored frozen at −70°. This comprises the source tissue for enzyme extraction.

The frozen cotyledons are powdered in a stainless steel mortar and pestle at approximately −70°, and the powder is stored under liquid nitrogen or at −70° until required. Extraction is accomplished by adding, at 0°–4°, to the powder 4 ml/g of "extraction buffer" comprising 50 mM $KH_2PO_4$-KOH pH 6.9, 5 mM ethylenediamine tetraacetate (EDTA), 2 mM DTT, 1 mM sodium ascorbate, 1 mM phenylmethylsulfonyl fluoride, 1 $\mu$M leupeptin, and 1 $\mu$M pepstatin. The stirred mixture of powder and buffer is blended in a motorized macerator (Brinkmann (Westbury, N.Y.) "Polytron", three bursts of 45 sec each) and then filtered through four layers of cheesecloth. This and all subsequent steps are conducted at 0°–4°. The resulting filtrate is centrifuged at approximately 14,000 xg (max.) for 30 min. The supernatant fractions are filtered through "Miracloth" (Calbiochem. Corp., LaJolla, Calif.) and the resulting liquid is referred to as the "crude extract".

The crude extract is subjected to ammonium sulfate fractionation as follows. Sufficient solid ammonium sulfate is gradually added with stirring over 30 min to achieve 70% saturation. The preparation is then stirred for a further 30 min. After centrifuging as described above, the pelleted material is resuspended in extraction buffer (2 ml/g original tissue weight) and stirred for 10 min until dissolved. Ammonium sulfate is then added as before, but this time only sufficient to achieve 50% saturation. After centrifuging as before, the supernatant fraction is discarded. The pelleted material, which contains the C12-preferring acyl-ACP thioesterase, may be frozen by immersion in liquid nitrogen and then stored at −70° at this stage if desired. The resulting material is referred to as the "ammonium sulfate fraction." Very little of the C12-preferring acyl-ACP thioesterase activity is lost if the pellet is frozen very rapidly.

After thawing to 4° if necessary, the pellet material is resuspended in "HA1 buffer" (1 ml/g original tissue weight), comprising 50 mM $KH_2PO_4$-KOH pH 6.9, 25% w/v glycerol, 1 mM DTT. The resuspended preparation is placed in dialysis tubing (12,000–14,000 molecular weight cutoff) and set to dialyze against HA1 buffer. (Typically a preparation from 600 g of cotyledon tissue will require two successive dialysis steps against 4 liters of buffer each, for at least three hours each.) Before application to the first column, the dialyzed material is centrifuged as described above and the pelleted material is discarded.

The supernatant material from post-dialysis centrifugation is applied to a column of hydroxyapatite (HA-Ultrogel from IBF Biotechnics, catalog. no. 247741, Savage, Md.; for a preparation from 500–1200 g of tissue typically 10 cm diameter × 12.5 cm bed height), equilibrated in HA1 buffer. The column is then washed with HA1 buffer until the absorbance of the effluent at 280 nm no longer changes. A considerable amount of protein and sometimes a small amount of the C12-preferring acyl-ACP thioesterase activity fail to bind the column and are washed through it. The bulk of the C12-preferring acyl-ACP thioesterase activity binds, and is eluted by applying "HA2 buffer" comprising 400 mM $KH_2PO_4$-KOH pH 6.9, 25% w/v glycerol, 1 mM DTT. The effluent is collected in fractions (5–10 ml in volume), which are then assayed for C12-preferring acyl-ACP thioesterase activity. The active fractions are combined and dialyzed as described above, against "CM1 buffer" comprising 5 mM $KH_2PO_4$-KOH pH 6.5, 25% w/v glycerol, 1 mM EDTA, 1 mM DTT (typically three dialysis periods of at least 3 hr each against 4 liters each). After dialysis the material is clarified by centrifugation as described previously, the pellets being discarded.

The supernatant fraction is then applied to a cation exchange column (Pharmacia CM-Sepharose Fast Flow, Piscataway, N.J., catalog no. 17-0719-01, 10 cm diameter × 14 cm bed height) equilibrated with CM1 buffer. After loading, the column is washed with CM1 buffer until the absorbance of the effluent stream at 280 nm no longer changes. A considerable quantity of protein and a significant amount (e.g. 50%) of the C12-preferring acyl-ACP thioesterase activity fail to bind the column and are washed through it. This partial binding of the C12-preferring acyl-ACP thioesterase has been investigated and found to result from aggregation of this enzyme with other, unidentified proteins at the time of extraction. In effect there are two populations of the C12-preferring acyl-ACP thioesterase up to this point in the purification scheme, free enzyme and aggregate. The cation exchange column separates these two forms and the aggregate is discarded. The unaggregated form of the C12 acyl-ACP thioesterase is eluted from the column by applying "CM2 buffer" comprising 50 mM $KH_2PO_4$-KOH pH 6.9, 150 mM NaCl, 25% w/v glycerol, 1 mM EDTA, 1 mM DTT. The effluent stream is fractionated and assayed as before, and the active fraction are pooled and dialyzed against "ACP1 buffer" comprising 10 mM $KH_2PO_4$-KOH pH 6.5, 150 mM NaCl, 25% w/v glycerol, 1 mM EDTA, 1 mM DTT, 0.1% w/v 3-[(3-cholamidopropyl)-dimethylammonio]-1-propanesulfonate (CHAPS). Typically two successive dialyses for at least 3 hr each, against 4 liters each, suffice for a preparation from 600 g tissue.

The dialyzed material is then applied to a column of immobilized ACP (2.5 cm diameter × 10.5 cm bed height). This column is manufactured by coupling *Escherichia coli* ACP to cyanogen bromide-activated Sepharose 4B according to instructions supplied by the manufacturer of this column packing (Pharmacia Inc., Piscataway, N.J.). The *E. coli* ACP is prepared as referenced in Example 1. Before use the column is equilibrated with ACP1 buffer. The dialyzed material from the cation exchange column is applied at 1–1.3 ml/min, and fractions of 8 ml volume are collected throughout the procedure. Fractions are assayed for C12-preferring acyl-ACP thioesterase activity, and for total protein content using a CoomassieBBlue assay method (BioRad Inc., Richmond, Calif., catalog no. 500–0001). A substantial amount of protein washes through the column without binding. Almost all of the C12-preferring acyl-ACP thioesterase activity binds. The column is washed with ACP1 buffer until the protein assay detects no more protein in the effluent stream. It is then washed with "ACP2 buffer" comprising 50 mM $KH_2PO_4$-KOH pH 8.5, 50 mM glycine, 25% w/v glycerol, 1 mM EDTA, 1 mM DTT, 0.1% w/v CHAPS. This high pH wash serves to remove nonspecifically bound protein. A small amount of C12 acyl-ACP thioesterase activity is occasionally co-eluted with it. After the protein assay has again indicated that no more protein is being eluted, a linear "elution gradient" is applied. This comprises 560ml combined volume of "ACP3 buffer" (100 mM $KH_2PO_4$-KOH pH 6.9, 25% w/v glycerol, 1 mM EDTA, 1 mM DTT, 0.1% w/v CHAPS) and "ACP4 buffer" (500 mM $KH_2PO_4$-KOH pH 6.9, 25% w/v glycerol, 1 mM EDTA, 1 mM DTT, 0.1% w/v CHAPS). If C12-preferring acyl-ACP thioesterase activity is still eluting from the column when the gradient ends, its elution can be completed by applying more ACP4 buffer. The collected fractions are assayed as before, and a second C12-preferring acyl-ACP thioesterase assay is also performed with the fractions diluted fifty-fold. By compensating for nonlinearity of the assay this gives a more precise location of the maximum enzyme activity. The C12-preferring acyl-ACP thioesterase activity is typically present in the gradient-eluted fractions as two peaks, a smaller one eluting just before a much larger one.

The fractions comprising each peak are pooled separately. The larger, later eluting peak is the most pure material that is used for subsequent experiments, protein sequencing etc. Analysis of this material by typical SDS-PAGE procedures shows only 5–6 strongly staining bands and a few weakly staining ones.

EXAMPLE 3—C12-Preferring Acyl-ACP Thioesterase Inhibitor Studies

Table 1 below reports inhibition of Bay cotyledon C12-preferring acyl-ACP thioesterase by thiol reagents observed when an ammonium sulfate fraction (see, Example 2) was assayed (see, Example 1).

TABLE 1

| Addition to Assay | Mean Activity* | Percent Inhibition |
| --- | --- | --- |
| None (control) | 4322 | — |
| 0.5 mM iodoacetamide | 4180 | 3 |
| 5 mM | 4047 | 6 |
| 0.5 mM N-ethylmaleinide | 4320 | 0 |
| 5 mM | 103 | 98 |

*"Mean Activity" is a measurement of the mean score of duplicates provided in cpm as observed in the ether layer of Example 1

After removal of dithiothreitol from an ammonium sulfate fraction preparation by passage through a small column of G25-50 gel filtration medium (Pharmacia, Piscataway, N.J.) the following assay results were observed.

TABLE 2

| Addition to Assay | Mean Activity* | Percent Inhibition |
| --- | --- | --- |
| None (control) | 3776 | — |
| 5 mM iodoacetamide | 3851 | 0 |
| 5 mM N-ethylmaleimide | 269 | 93 |

*"Mean Activity" is a measurement of the mean score of duplicates provided in cpm as observed in the ether layer of Example 1

These preliminary inhibitor studies indicate that the Bay C12-preferring acyl-ACP thioesterase is insensitive to 5 mM iodoacetamide and almost completely inhibited by 5 mM N-ethylmaleimide. These results suggest that C12-preferring acyl-ACP thioesterase is an "active thiol" type of esterase rather than an "active serine" type.

EXAMPLE 4—"Bay C12-Preferring Acyl-ACP Thioesterase Substrate Specificity as a Function of Chain Length In tests comparing activity of the amonium sulfate fraction preparations of Bay C12-preferring acyl-ACP thioesterase of Example 2 against various length medium-chain fatty acids in the assay of Example 1, the greatest activity has been manifest towards C12-ACP over C8, C10, C12, C14 and C16 ACP substrates as shown in Table 3.

TABLE 3

| Acyl-ACP acyl Chain length | Relative Thioesterase Activity* |
| --- | --- |
| 8 | 1.0 |
| 10 | 2.7 |
| 11 | 3.7 |
| 12 | 24.0 |
| 14 | 4.0 |
| 16 | 4.7 |

*C8-ACP activity set to 1.0

EXAMPLE 15—Bay C12-Preferring Thioesterase Substrate Specificity as a Function of ACP Versus CoA Crude extracts of Bay cotyledons hydrolyze lauroyl coenzyme A (CoA) as well as lauroyl-ACP. This is due to the presence of separate enzymes acting respectively on these substrates, i.e. to C12-preferring acyl-ACP thioesterase acting on lauroyl-ACP and another enzyme acting on lauroyl CoA. The distinct nature of these enzymes is indicated by their separation at the ACP column stage in the purification scheme. Lauroyl-CoA hydrolysis activity is found chiefly in the material which fails to bind the ACP column, and C12-preferring acyl-ACP thioesterase activity is found in the material which binds and which is subsequently eluted with a phosphate concentration gradient. Activities of the peak fraction of unbound and bound material serves to illustrate this separation, as shown in the following table.

TABLE 4

| Fraction | Activity on C12-CoA Substrate* | Activity on C12-ACP Substrate* |
| --- | --- | --- |
| Flow-through (nonbinding) | 10808 | 300 |
| Gradient-eluted | 27 | 2772 |

*cpm of ether-extractable product

Therefore, the Bay C12-preferring acyl-ACP thioesterase shows much more activity towards lauroyl-ACP than towards lauroyl-CoA.

EXAMPLE 6—Role of the Enzyme in Laurate Production

Further evidence that the C12-preferring acyl-ACP thioesterase is involved in the biosynthesis of laurate groups that predominate in the Bay seeds comes from a comparison of the extractable activity of the enzyme at two different stages of seed development. As shown in the following table, Table 5, very young seeds, which contain only long-chain fatty acids and insignificant amounts of laurate, yield much less C12-preferring ACP thioesterase than older seeds that have accumulated significant amounts of laurate. Thus it appears that significant activity of this enzyme is only present when the seeds are accumulating laurate. Additionally, there appears to be much less difference in lauroyl-CoA hydrolysis activity, consistent with their being different enzymes as discussed above in Example 5.

TABLE 5

| Tissue Source | C12 acyl-CoA Hydrolysis Activity In Assays* | C12 acyl-ACP Thioesterase Activity In Assays* |
| --- | --- | --- |
| Normal Seeds (≈ 2 g/cotyledon pair) | 31,268 | 4704 |
| Young Seeds (≈ 0.5 g/cotyledon | 29,995 | 376 |

TABLE 5-continued

| Tissue Source | C12 acyl-CoA Hydrolysis Activity In Assays* | C12 acyl-ACP Thioesterase Activity In Assays* |
|---|---|---|
| pair) | | |

*cpm ether-extractable radioactivity

EXAMPLE 7—In Vitro Bay Fatty Acid Synthesis Assay

An ammonium sulfate fraction of a Bay embryo extract will synthesize the same specific fatty acids as those found in the maturing seed if supplied with E. coli ACP, malonyl-CoA, and other typical cofactor and substrate requirements of documented in vitro fatty acid synthesizing systems (Jaworski, et al., Arch. Biochem. Biophys. (1974) 163:769-776). The products of this in vitro activity include water-soluble octanoyl and decanoyl esters but almost undetectable water-soluble lauroyl ester, even though laurate is the major free fatty acid product. These results are most simply explained in terms of the fatty acid synthesizing system producing acyl-ACP's of successively increased chain length, and the specific lauroyl-ACP thioesterase intercepting the acyl-ACP when the acyl moiety has been extended as far as twelve carbon atoms, by hydrolyzing apart the acyl and ACP moieties at that stage.

EXAMPLE 8—Cuphea Assay

Following the same general procedures as outlined in Example 1, to assay for C10 thioesterase activity, the following mixture is incubated at 30° for 10-60 min: 20 μl extract of immature Cuphea hookeriana seeds in the "extraction buffer" described in Example 9, and approximately 250 pmol of [$^{14}$C]-radiolabeled acyl-ACP substrate, (usually decanoyl-ACP is labeled in the carboxylate group to 50-60 μCi/μmol) in a total volume of 50 μl, for a final decanoyl-ACP concentration of 0.5-5.0 μM, typically 5.0 μM. The reaction is stopped by adding 0.5ml 10% (v/v) cold (4°) acetic acid and placing the reaction mixture on ice for a few minutes. The fatty acid product of the hydrolytic enzyme action is extracted away from the unhydrolyzed substrate by adding 2 ml diethyl ether and mixing vigorously. The ether is transferred to 5 ml scintillation fluid for scintillation counting. Additional ether extracts may be performed to recover remaining traces of product for more accurate quantitation of the activity if desired.

EXAMPLE 9—Cuphea C10-Preferring Acyl-ACP Thioesterase Purification and Identification Immature seeds of Cuphea hookeriana are harvested. The total fatty acid composition of a few of the harvested seeds is analyzed by standard techniques to make sure that they are at the correct stage of development. This is defined as the stage at which octanoate and decanoate predominate in the fatty acyl composition. The harvested seeds are stored frozen at −70°. This comprises the source tissue for enzyme extraction.

An acetone powder is prepared by grinding the seeds to a powder in a mortar and pestle under liquid nitrogen, and then grinding the powder in a mortar and pestle with cold acetone (at approximately −20°). The powder is collected by filtration and rinsed with cold ether to remove remaining traces of acetone. It is then extracted with 10 ml of "extraction buffer" per gram of acetone powder weight (this and all subsequent steps at 0°-4°) comprising 50 mM $KH_2PO_4$-KOH pH 7.5, 10 mM 2-mercaptoethanol. The homogenate is centrifuged at 11,000 xg for 15 min at 4°, and the supernatant fraction used for subsequent purification steps after filtration through two layers of Miracloth (Calbiochem. Inc.; LaJolla, Calif.).

The supernatant fraction is then subjected to ammonium sulfate fractionation. The 40-60% saturation ammonium sulfate pellet (prepared as described in Example 2) is redissolved in "buffer" comprising 50 mM $KH_2PO_4$-KOH pH 6.9, 10% (v/v) glycerol, and 10 mM 2-mercaptoethanol, and dialyzed against this buffer to remove remaining ammonium sulfate.

The resulting preparation is then subjected to hydroxyapatite column chromatography. The following method applies to ammonium sulfate fraction from 100 g fresh weight of starting seed tissue. The dialyzed ammonium sulfate fraction (35-40 ml) is applied to a column of hydroxyapatite (2.5 cm × 14cm bed height of Bio-Gel HTP from Bio-Rad Inc.; Richmond, Calif., catalog no. 130-0420), equilibrated in 50 mM $KH_2PO_4$-KOH pH 6.9, 10% (v/v) glycerol, 4 mM 2-mercaptoethanol. The column is then washed (flow rate 1.5 ml/min throughout) with 280 ml of the same buffer. Elution is accomplished with a 580 ml linear gradient from these conditions to 350 mM $KH_2PO_4$-KOH pH 6.9, 10% (v/v) glycerol, 4 mM 2-mercaptoethanol, collecting fractions of 12 ml volume. The eluted fractions are assayed for hydrolase activity using decanoyl-ACP as substrate.

Two peaks of activity are obtained, one passing through the column without binding, and the other binding and being subsequently eluted with the phosphate gradient. Both peaks from the hydroxyapatite column contain hydrolytic activity towards long-chain substrates (acyl group of 14 or more carbon atoms). As far as the medium-chain substrates are concerned, the flow-through peak shows little preference, whereas the gradient peak shows considerable preference for decanoyl-ACP (See, Example 12).

At an early stage in the partial purification, when buffered with 100 mM HEPES, the decanoyl-ACP CIO-preferring acyl-ACP thioesterase shows considerable tolerance of assay pH, activity changing minimally between pH 6.5 and 8.5, with a maximum at pH 7.5. In contrast there is sensitivity to ionic strength in the assay, e.g. using potassium phosphate as the assay buffer activity declines as the phosphate concentration is raised, although activity is still detectable in 350 mM phosphate.

The C10-preferring acyl-ACP thioesterase activity and other proteins in the partially purified preparations are lowered in concentration by extensive contact with glass and plastic surfaces. This effect is reduced by the inclusion of detergents such as Triton X100 or CHAPS in the column and assay buffers. Some detergents are stimulatory in the assay.

The C10-preferring acyl-ACP thioesterase activity is rapidly lost during the ammonium sulfate precipitation step of purification unless 2-mercaptoethanol is present in the buffers as described above. In the buffers described the activity is very stable both at 0° and during repeated freezing to −20° or −70°.

EXAMPLE 10—C10 Acyl-ACP Thioesterase Inhibitor Studies

Preliminary inhibitor studies indicate that the Cuphea C10-preferring acyl-ACP thioesterase is insensitive to phenylmethylsulfonyl fluoride, insensitive to iodoacetamide, and completely inhibited by 5 mM N-ethylmaleimide. This suggests that it is an "active thiol" type of esterase rather than an "active serine" type.

EXAMPLE 11—Plant Thioesterase Sequencing

In this example, amino acid and nucleic acid sequencing of the Bay C12-preferring acyl-ACP thioesterase is described. This technique may also be employed for the sequencing of other plant thioesterases of this invention as well.

A sample of thioesterase purified through the ACP-Sepharose step is prepared for proteolytic digestion and sequencing. The sample (12 µg of thioesterase in 80 µl) is denatured and reduced by heating to 95° C. for 5 minutes in 160 µl of Andersons' sample buffer (Anderson & Anderson, *Anal. Biochem.* (1978) 85:331–340) containing 2% sodium dodecyl sulfate, 5% β-mercaptoethanol, 20% glycerol, 2% 3/10 ampholytes, and 2% Triton X-100. Proteins in 20 µl aliquots 1 µg total protein in each) are separated by two-dimensional electrophoresis as described by Anderson and Anderson (*Anal. Biochem.* (1978) 85:331–340 and 341–354), except that the second dimension slab gel is 1.5 mm in thickness. After the second dimension electrophoresis, each of the slab gels is removed and proteins within the gel are blotted directly to a nitrocellulose membrane in a transblot system (Bio-Rad, Richmond, Calif.) using the method of Towbin et al (*Proc. Nat. Acad. Sci. USA* (1979) 76:4350–4354). The protein spots on the membrane are detected by reversible staining with Ponceau S (Sigma, St. Louis, Mo.) as described by Salinovich and Montelaro (*Anal. Biochem.* (1986) 156:341–347). Alternatively the spots may be detected by staining with amidoblack (Schaffner and Weissman, Anal. Biochem. (1973).56:502–514).

For preparations of thioesterase having undergone an additional chromatographic purification step, one-dimensional polyacrylamide gel electrophoresis is sufficient to produce protein pure enough for sequencing. In this case, the sample (12 µg of thioesterase in 80 µl) is reduced and denatured by heating to 95° C. for 5 min with 20 µl of a sample buffer containing 25% (vol/vol) glycerol, 2.5% (wt/vol) sodium dodecyl sulfate (SDS), and 25% (vol/vol) β-mercaptoethanol in 0.156M Tris-HCl, pH 6.8. Proteins in separate aliquots (30–35 µl) of the sample are separated by one-dimensional electrophoresis as described by Laemmli (Nature (1970) 227:680–685), one aliquot per 1-cm lane on a 1.5 mm thick gel. After completion of the electrophoresis, the gel is removed, blotted, and thereafter the samples are treated as described for the two-dimensional case.

In preparation for digestion, spots corresponding to thioesterase protein are cut out of each of the membrane blots and are pooled together in a 5-ml plastic test tube. The methods of treatment and digestion have been described by Aebersold et al (Proc. Nat'l Acad Sci. U.S.A. 84:6970–6974)). The membrane pieces are treated for 30 min at 37° C. with 1.2 ml of freshly prepared 0.5% (weight/vol) polyvinylpyrrolidone with average molecular weight of 40,000 (PVP-40, Aldrich, Milwaukee, Wis.) dissolved in 100 mM acetic acid. The excess PVP-40 is removed by several washes with 3 ml of water, removal of PvP-40 is complete when the absorbance at 214 nm of successive washes no longer decreases. The pieces are then removed from the wash tube, and are placed in a 1 -ml Eppendorf plastic tube, and 100 mM Tris-HCl, pH 8.2/acetonitrile, 95:5 (vol/vol) is added so that the liquid just covers the top of them. The digest is started by addition of 10 µl of Boehringer Mannheim sequence grade trypsin (100 µg/ml solution in 1% HCl) is added, and the sample is allowed to digest at 37° C. for 24 h, with occasional stirring. The amount of protease added is usually between 1/20 and 1/10 of the weight of protein being digested. Peptides elute from the membrane into the digest buffer during the incubation. The digestion is terminated by addition of 10 µl of 10% (vol/vol) trifluoroacetic acid (TFA).

Alternatively the chips may be suspended in 100 mM sodium phsophate, pH 7.8/acetonitrile, 95:5 (vol/vol), and digested for 24 hours at 25° C. with 10 µl of Boehringer Mannheim sequence grade endoproteinase gluC (100 µg/ml solution in water). Digestion with trypsin allows cleavage at lysine and arginine residues, whereas digestion with gluC cleaves at aspartic acid and glutamic acid residues under its respective conditions. Digestion of separate samples with each of the proteases affords identification of overlapping peptides and construction of longer peptide sequences useful for PCR technology.

Separation of the released peptides is accomplished through reverse-phase HPLC on a C18 (2×150 mm) column using a 120-min gradient increasing from 7% to 70% acetonitrile in 0.1% TFA at a flow rate of 50 µl per min. The elution of peptides is monitored by absorbance at 214 nm, each peptide being collected into a separate fraction tube. The peptides are stored frozen at −20° C. until application to the protein sequencer (Applied Biosystems, Foster City, Calif.).

Alternatively, the peptides may be alkylated before separation on HPLC. Alkylation allows identification of cysteine residues on the sequencer, which otherwise go undetected. The unacidified digest mixture is reduced by addition of 1 µl of 10% (vol/vol) µ-mercaptoethanol (1.43 µmol) and incubated at 37° C. for 2 hours. The reduced peptides are then alkylated with 1.6 µmol of [$^3$H]-iodoacetic acid (200 mCi/mmol) for 30 min at room temperature in the dark. The mixture is then acidified with 10 mµl of 10% (vol/vol) TFA, applied to the reverse-phase HPLC column and further treated as described above. Other alkylating agents may be used including iodoacetamide and 4-vinylpyridine. The latter reagent leads to formation of pyridylethyl-cysteine residues which are identifiable on the protein sequencer by the unique retention time of its corresponding PTH-amino acid derivative.

Once partial amino acid sequences are determined, they may be used to obtain DNA sequence of the plant thioesterase via Polymerase Chain Reaction (PCR) technology. Thus, four oligonucleotide fragments are synthesized on an Applied Biosystems model 380A DNA synthesizer to amino acid sequences which have the least redundancy for use as PCR primers. Restriction sites are designed into the ends of the oligonucleotide primers so that the resulting DNA fragments may be readily manipulated in cloning. Purified genomic DNA isolated from the plant thioesterase source are used as templates in reaction.

PCR reactions are run using Taq polymerase (Gene Amp Kit) and the DNA termal cycler (Perkin-Elmer/Cetus) in four different combinations of the oligonucleotides as 5'- or 3'- primers. The resulting DNA products are run on an agarose gel for separation. DNA sequences are determined by the dideoxy-chain terminatino method of Sanger et. al, *Proc. Natl. Acad. Sci. USA* (1977) 74:5463–5467) using the 7-Deaza-dGTP Reagent Kit with Sequenase version 2 Enzyme (United States Biochemical Corp., Cleveland, Ohio). The sequence data are analyyzed using the IntelliGenetics Suite of molecular programs Gel and SEQ.

EXAMPLE 12—Cuphea C10 Acyl ACP Thioesterase Substrate Specificity as a Function of Chain Length The substrate specificity of Cuphea C10 acyl-ACP thioesterase towards medium-chain acyl-ACP's has been determined at the hydroxyapatite stage in purification, as described in Example 10:

| Substrate | Hydrolysis Activity (mean) (pmol/min) |
| --- | --- |
| C6-ACP | 188 |
| C8-ACP | 485 |
| C10-ACP | 6950 |
| C11-ACP | 649 |
| C12-ACP | 1032 |
| C14-ACP | 4055 |

The activity towards the longer-chain substrate 14:0-ACP is considered to be due to the presence of long-chain thioesterase activity, analogous to long-chain thioesterases of safflower seed and avocado mesocarp tissue that are described in published literature. Assay of the preparation with the preferred substrate of such an enzyme, 18:1-ACP, indicates the presence of substantial activity, consistent with this hypothesis. The activity towards 10:0-ACP and the smaller amount of activity towards 8:0-ACP indicate the presence of the medium-chain-specific thioesterase responsible for medium-chain fatty acid production in developing Cuphea hookeriana seeds.

The reactions catalyzed have been shown to be simple hydrolysis. The ether-extracted products of both "time zero" reactions and one hour reactions with 6:0-ACP, 8:0-ACP, and 10:0-ACP substrates were chromatographed on silica G thin-layer plates (mobile phase: hexane/diethyl ether/acetic acid, 80:20:1 v/v) to determine the lipid class. Lauric acid was added as unlabeled carrier to inhibit evaporation of liberated short-chain free fatty acids. Tricaprin, dicaprin, monocaprin, and lauric acid were used as standards. The TLC plate was developed half-way and then air dried for 5 minutes. The plate was then returned to the tank and development was completed to within 1 cm of the top of the plate. The developed plate was dried and then scanned for 800 mins on an AMBIS radiochromatogram scanner to quantitate radiolabeled spots. Following scanning, the plate was stained in iodine vapor for 15 minutes to visualize the lipids. The principal radiolabeled products co-migrated with the free fatty acids, and were substantially more radioactive in the samples incubated for 1 hour compared with the zero-time controls.

To verify that the chain lengths of the products were those of the corresponding substrates, the ether-extracted products (with an unlabeled free fatty acid mixture as carrier) were neutralized to phenolphthalein endpoint with KOH and then derivatized with bromphenacyl bromide and chromatographed by reverse-phase HPLC. A C18 column was used in conjunction with an acetonitrile/water gradient. In all cases, only one chain length of product was observed, identical to the substrate chain length.

EXAMPLE 14—Transformation with Plant Thioesterase

A variety of methods have been developed to insert a DNA sequence of interest into the genome of a plant host to obtain the transcription or transcription and translation of the sequence to effect phenotypic changes.

Brassica Transformation

Seeds of Brassica napus cv. Westar are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyriodoxine (50 µg/l), nicotinic acid (50 µg/l), glycine (200 µg/l), and 0.6% Phytagar (Gibco) pH 5.8. Seeds are germinated in a Percival chamber at 22° C. in a 16 h photoperiod with cool fluorescent and red light of intensity approximately 65 µ Einstein per square meter per second ($\mu Em^{-2}S^{-1}$).

Hypocotyls are excised from 5-7 day old seedlings, cut into pieces approximately 4 mm in length, and plated on feeder plates (Horsch et al., Science (1985) 227:1229-1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg KH$_2$PO$_4$ with 3% sucrose, 2,4-D (1.0 mg/1), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MSO/1/0 medium. All hypocotyl explants are preincubated on feeder plates for 24 h. at 22° C. in continuous light of intensity 30 $\mu Em^{-2}S^{-1}$ to 65 $\mu EM^{-2}S^{-1}$.

Single colonies of A. tumefaciens strain EHA 101 containing a binary plasmid are transferred to 5 ml MG/L broth and grown overnight at 30° C. Hypocotyl explants are immersed in 7-12 ml MG/L broth with bacteria diluted to 1×10$^8$ bacteria/ml and after 10-25 min. are placed onto feeder plates. Per liter MG/L broth contains 5 g mannitol, 1 g L-Glutamic acid or 1.15 g sodium glutamate, 0.25 g kH$_2$PO$_4$, 0.10 g NaCL, 0.10 g MGSO$_4$·7H$_2$O, 1 mg biotin, 5 g tryptone, and 2.5 g yeast extract, and the broth is adjusted to pH 7.0. After 48 h of co-incubation with Agrobacterium, the hypocotyl explants are transferred to B5 0/1/0 callus induction medium which contains filter sterilized carbenicillin (500 mg/1, added after autoclaving) and kanamycin sulfate (Boehringer Mannheim; Indianapolis, Ind.) at concentrations of 25 mg/1.

After 3-7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l ) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for thioesterase activity.

Peanut Transformation

DNA sequences of interest may be introduced as expression cassettes, comprising at least a promoter region, a gene of interest, and a termination region, into a plant genome via particle bombardment as described in European Patent Application 332 855 and in co-pending application U.S. Ser. No. 07/225,332, filed Jul. 27, 1988.

Briefly, tungsten or gold particles of a size ranging from 0.5 $\mu$M–3 $\mu$M are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers.

The bomardment of the tissue with the DNA-coated particles is carried out using a Biolistics TM particle gun (Dupont; Wilmington, Del.). The particles are placed in the barrel at variable distances ranging from 1 cm–14cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 $\mu$M to 300 $\mu$M.

Following bombardment, plants may be regenerated following the method of Atreya, et al., (*Plant Science Letters* (1984) 34:379–383). Briefly, embryo axis tissue or cotyledon segements are placed on MS medium (Murashige and Skoog, Physio. Plant. (1962) 15:473) (MS plus 2.0 mg.1 6-benzyladenine (BA) for the cotyledon segments) and incubated in the dark for 1 week at 25°±2° C. and are subsequently transferred to continuous cool white fluorescent light (6.8 W/m$^2$). On the 10th day of culture, the plantlets are transferred to pots containing sterile soil, are kept in the shade for 3–5 days are and finally moved to greenhouse.

The putative transgenic shoots are rooted. Integration of exogenous DNA into the plant genome may be confirmed by various methods know to those skilled in the art.

By the above examples, demonstration of critical factors in the production of medium-chain fatty acids is described. A protocol is provided to obtain partially purified C12-acyl ACP thioesterase from the California Bay, various properties of the protein are described including methods to obtain and use amino acid and nucleic acid sequence related thereto. In addition, methods to obtain a partially purified preparation of a C10 acyl-ACP thioesterase from *Cuphea hookeriana* is also provided. Through this invention, one can obtain the amino acid and DNA sequences which encode the thioesterase for a variety of applications.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practised within the scope of the appended claim.

What is claimed is:

1. A plant thioesterase being substantially purified from other proteins of said plant and having preferential hydrolase activity toward C12 acyl-ACP substrate.

2. The thioesterase of claim 1 obtainable from an immature plant embryo.

3. The thioesterase of claim 1 obtainable from Lauraceae.

4. The thioesterase of claim 3 wherein said thioesterase is *Umbellularia californica* C12-preferring acyl-ACP thioesterase.

.5. A plant thioesterase protein characterized as:
  (i) free from intact cells of said plant;
  (ii) capable of catalyzing the production of laurate and ACP from lauroyl-ACP;
  (iii) having preferential activity toward a lauroyl-ACP substrate as compared to a palmitoyl-ACP substrate;
  (iv) having preferential activity toward a lauroyl-ACP substrate as compared to a lauroyl-CoA substrate; and
  (v) an active thiol type esterase.

6. A C12-preferring acyl-ACP thioesterase obtainable from a plant, wherein said thioesterase is substantially free from a long chain acyl-ACP thioesterase of said plant.

7. An *Umbellularia californica* medium-chain acyl-ACP thioesterase wherein said thioesterase is substantially free from other fatty acid synthetase proteins of said *Umbellularia californica*, said medium-chain thioesterase being characterized as capable of being purified by:
  (i) preparing a crude extract from ground *Umbellularia californica* immature embryos;
  (ii) subjecting said crude extract to ammonium sulfate fractionation;
  (iii) recovering and resuspending the pellet from said ammonium sulfate fractionation;
  (iv) subjecting said resuspended pellet to hydroxyapatite column chromatography and collecting the eluted thioesterase active fractions;
  (v) applying said active fractions to a cation exchange column and collecting the eluted fractions having thioesterase activity;
  (iv) applying said eluted fractions having thioesterase activity to an immobilized ACP column; and
  (vii) recovering the C12 preferring acyl-ACP thioesterase fractions eluted from said ACP column.

8. The *Umbellularia californica* medium-chain acyl-ACP thioesterease of claim 7, wherein said medium-chain acyl-ACP thioesterase is further characterized as:
  (i) capable of catalyzing the production of laurate and ACP from lauroyl-ACP;

(ii) having preferential activity toward a lauroyl-ACP substrate as compared to a palmitoyl-ACP substrate;

(iii) having preferential activity toward a lauroyl-ACP substrate as compared to a lauroyl-CoA substrate; and (iv) an active thiol type esterase.

9. The thioesterase of claim 5 or 6 obtainable from an immautre plant embryo.

10. The thioesterase of claim 5 or 6 obtainable from Lauraceae.

11. The thioesterase of claim 5 or 6 wherein said thioesterase is *Umbellularia californica* C12-preferring acyl-ACP thioesterase.

* * * * *